United States Patent
Bulent et al.

(10) Patent No.: US 10,124,102 B2
(45) Date of Patent: Nov. 13, 2018

(54) ENDOVASCULAR PERMANENT HEART ASSIST DEVICE

(71) Applicants: Oran Bulent, Konya (TR); Oran Omer Faruk, Konya (TR); Avci Elif Oran, Konya (TR)

(72) Inventors: Oran Bulent, Konya (TR); Oran Omer Faruk, Konya (TR); Avci Elif Oran, Konya (TR)

( * ) Notice: Subject to any disclaimer, the term of this patent is extended or adjusted under 35 U.S.C. 154(b) by 0 days.

(21) Appl. No.: 14/648,912

(22) PCT Filed: Dec. 18, 2013

(86) PCT No.: PCT/TR2013/000372
§ 371 (c)(1),
(2) Date: Jun. 2, 2015

(87) PCT Pub. No.: WO2014/098780
PCT Pub. Date: Jun. 26, 2014

(65) Prior Publication Data
US 2015/0367050 A1    Dec. 24, 2015

(30) Foreign Application Priority Data
Dec. 20, 2012  (TR) ............... a 2012 15023

(51) Int. Cl.
| A61N 1/362 | (2006.01) |
| A61M 1/12 | (2006.01) |
| A61M 1/10 | (2006.01) |

(52) U.S. Cl.
CPC .......... *A61M 1/125* (2014.02); *A61M 1/1036* (2014.02); *A61M 1/12* (2013.01);
(Continued)

(58) Field of Classification Search
CPC .............. A61M 1/1015; A61M 1/1031; A61M 1/1036; A61M 1/12; A61M 1/125;
(Continued)

(56) References Cited

U.S. PATENT DOCUMENTS

| 5,527,159 A | * | 6/1996 | Bozeman, Jr. .......... A61M 1/10 415/900 |
| 5,613,935 A | * | 3/1997 | Jarvik .................... A61M 1/101 600/16 |

(Continued)

FOREIGN PATENT DOCUMENTS

| JP | S56145757 A | | 11/1981 |
| JP | 10070858 A | * | 3/1998 |
| TR | 2012/00951 A2 | | 9/2012 |
| WO | WO99/49912 A1 | | 10/1999 |
| WO | WO2009/091965 A1 | | 7/2009 |
| WO | WO2012/148367 A2 | | 11/2012 |

OTHER PUBLICATIONS

Peng Wu et al: "A self-bearing centrifugal blood pump based on induction motor with active and passive magnetic bearings", Fifth International Conference on Power Electronics and Drive Systems, Nov. 17, 2003, pp. 1642-1646, vol. 2, XP002722341, IEEE Piscataway, NJ, USA.

*Primary Examiner* — Lindsey G Wehrheim
(74) *Attorney, Agent, or Firm* — Gokalp Bayramoglu

(57) ABSTRACT

The invention is a heart assist device which has been developed in order to maintain the blood circulation in end-stage heart patients who do not respond to medical treatment, and it has been designed in size and shape so that it can be installed into the anatomically spacious root sections of the aorta and main pulmonary artery. With its small volume, and exceptional motor design without a shaft, the device, which contains a brushless, asynchronous and three-phase electric motor, will consume much less energy. The three-phase current required for the motor is provided from the power supply outside the body through the synchronous and wireless transmission of three phases. The (Continued)

invention is about a permanent endovascular cardiac support device which contains a three-phase, brushless, asynchronous electric motor, and the required energy is provided through the three-phase wireless power transmission from outside the body.

20 Claims, 7 Drawing Sheets

(52) U.S. Cl.
CPC .......... *A61M 1/101* (2013.01); *A61M 1/1005* (2014.02); *A61M 1/1013* (2014.02); *A61M 1/1015* (2014.02); *A61M 1/1031* (2014.02); *A61M 1/1086* (2013.01); *A61M 1/122* (2014.02); *A61M 1/127* (2013.01); *A61M 2205/0233* (2013.01); *A61M 2205/16* (2013.01); *A61M 2205/3334* (2013.01); *A61M 2205/8243* (2013.01); *A61M 2210/127* (2013.01)

(58) Field of Classification Search
CPC .......... A61M 1/127; A61M 2205/0233; A61M 2205/16; A61M 2210/127
See application file for complete search history.

(56) References Cited

U.S. PATENT DOCUMENTS

| | | | |
|---|---|---|---|
| 6,245,007 B1* | 6/2001 | Bedingham | A61M 1/101 600/16 |
| 7,144,364 B2* | 12/2006 | Barbut | A61F 2/90 600/16 |
| 2002/0012594 A1* | 1/2002 | Ozaki | F04D 13/0666 417/420 |
| 2003/0163019 A1 | 8/2003 | Goldowsky | |
| 2005/0225188 A1* | 10/2005 | Griepentrog | H01F 38/18 310/112 |
| 2006/0245959 A1* | 11/2006 | LaRose | F04D 3/02 417/423.5 |
| 2010/0076247 A1* | 3/2010 | Zilbershlag | A61M 1/1031 600/17 |
| 2010/0305692 A1 | 12/2010 | Thomas | |
| 2011/0178361 A1 | 7/2011 | Yomtov | |
| 2011/0184224 A1* | 7/2011 | Garrigue | A61M 1/101 600/16 |
| 2012/0146575 A1 | 6/2012 | Armstrong et al. | |
| 2012/0157753 A1 | 6/2012 | D'Ambrosio | |

* cited by examiner

ENDOVASCULAR PERMANENT HEART ASSIST DEVICE

TECHNICAL FIELD

The invention is about a new generation small heart assist device to be inserted into the ascending aorta and which has been developed in order to maintain blood circulation in the patients with severe heart failure. The device comprises a specially designed brushless electric motor and inside the rotor, which has no rotating shaft, propeller blades are located and they propel blood. Uninterruptible three-phase electrical power transmission, required to run this asynchronous three-phase motor, is provided from outside the body wirelessly. Since all electrical and electronic apparatus take place outside the patient's body, it is possible to update them easily. The invention is about a permanent new generation heart assist device placed into the major arteries and wider root partition of the major arteries.

BACKGROUND

Heart assist devices are vital devices in patients with end-stage heart diseases when heart muscle contractions are insufficient, and when no respond to medication is possible.

Nowadays, due to coronary heart diseases and infarcts (it is the formation of necrosis as a result of blockage of a coronary artery) tens of thousands of people receive the treatment of heart failure. When the drug treatment is insufficient, a heart transplant comes to the fore. Since finding a donor for a heart transplant is not very easy, heart assist devices kept ready for emergency use have become life-saving. In addition, some heart diseases may lead to heart failure even in newborn infants. For this reason, heart assist devices should be produced in all sizes, including pediatric sizes.

In order to ensure a high quality of life for the heart patients waiting for donor's heart, a number of studies to improve heart assist devices have been made and many different products have been presented to the physicians. Jarvik 2000, Lionheart, Coraide, HeartMate II (Thoratec Corp), Berlin heart and HeartSaver are some of these main products. The latest generation device in this area is DeBakey Heart assist device that has been developed with the help of NASA engineers in the United States by Micromed Company representing new generation devices. The fact that they are small in size and suitable for all ages have made these devices the most ideal for today. In addition, because it requires less invasive surgery, it is a matter of preference for cardiac surgeons as much as for the patients nowadays. Another similar device is the Heart-made heart assist device.

Formerly, balloon pumps inserted into the aorta were used for this purpose. It was intended that the balloon inflating and deflating synchronously with the heart would provide additional acceleration to the blood flow in the aorta. Later, air-driven systems were developed. Compressed air is provided from a compressor and an air tank moving with the patient. By moving back and forth when the compressed air inflates and deflates, the membrane produces a power propelling the blood. After a while, electric motor systems were developed, and these systems were first designed with an electric motor and a snail water turbine adapted to it. There are artificial blood vessels (conduits) entering and leaving the system. One end of the vessel is placed into the heart and the other end into the aortic artery, and when the engine runs, it takes blood from the heart and pumps out into the aorta. Compressed air systems were annoying as they run loudly. Because the efficiency of the engine was low and the engine volume was large in electric motor systems, it was a problem to install it into the patients. Moreover, considering them as high-energy-consuming systems, they significantly restricted the ability of the patients to move.

SUMMARY OF THE INVENTION

It is a heart assist device installed endovascularly into one or two of the large arteries such as the aorta (ascending aorta) and/or the main pulmonary arteries, and it is helpful to maintain the blood circulation in patients with severe heart failure. The rotor, which have no rotating shaft, and which rotates on a bearing roller supported with a magnetic bearing made of abrasion-proof materials such as ceramic and zirconium-like materials, provides adequate blood flow propelling the blood with its helical propeller blades. Since both the root portions of the main pulmonary artery and aorta after leaving the heart is anatomically broader, the assist device is in the size and shape that can be inserted into these wide parts.

Three-phase AC electrical voltage required for the electric motor is provided from outside the body through three separate wireless links. With the three-phase wireless power transmission, all three phases are simultaneously transmitted through three separate wireless links and the system is uninterruptedly fed from the three-phase power transmission apparatus outside the body. Thus all the electric and electronic apparatus, including microprocessor except the engine and power transmission apparatus are located not inside but outside the body, and hence it is possible to easily update and renew them every year. The technology for the engine and its power transmission apparatus, which remain inside the body, has not changed for years and is not expected to change in the forthcoming years. Therefore the engine and its power transmission apparatus will run for many years in the arteries of patients without requiring any update. In addition, the extra metal load in the patients body is avoided.

Simultaneously with electrocardiogram (ECG) signals, the rotor of the device rotates during the heart's contraction (systole) and stops or slows down during the relaxation (diastole). The device contains a sort of three-phase, brushless asynchronous servo electric motor using "direct drive technology". With its small volume, endovascular placement and exceptional design, the device will consume less energy and ensure longer battery life and it is presented as a different concept with new and outstanding features when compared with its counterparts in its field.

DETAILED DESCRIPTION OF THE INVENTION

Figure 1:
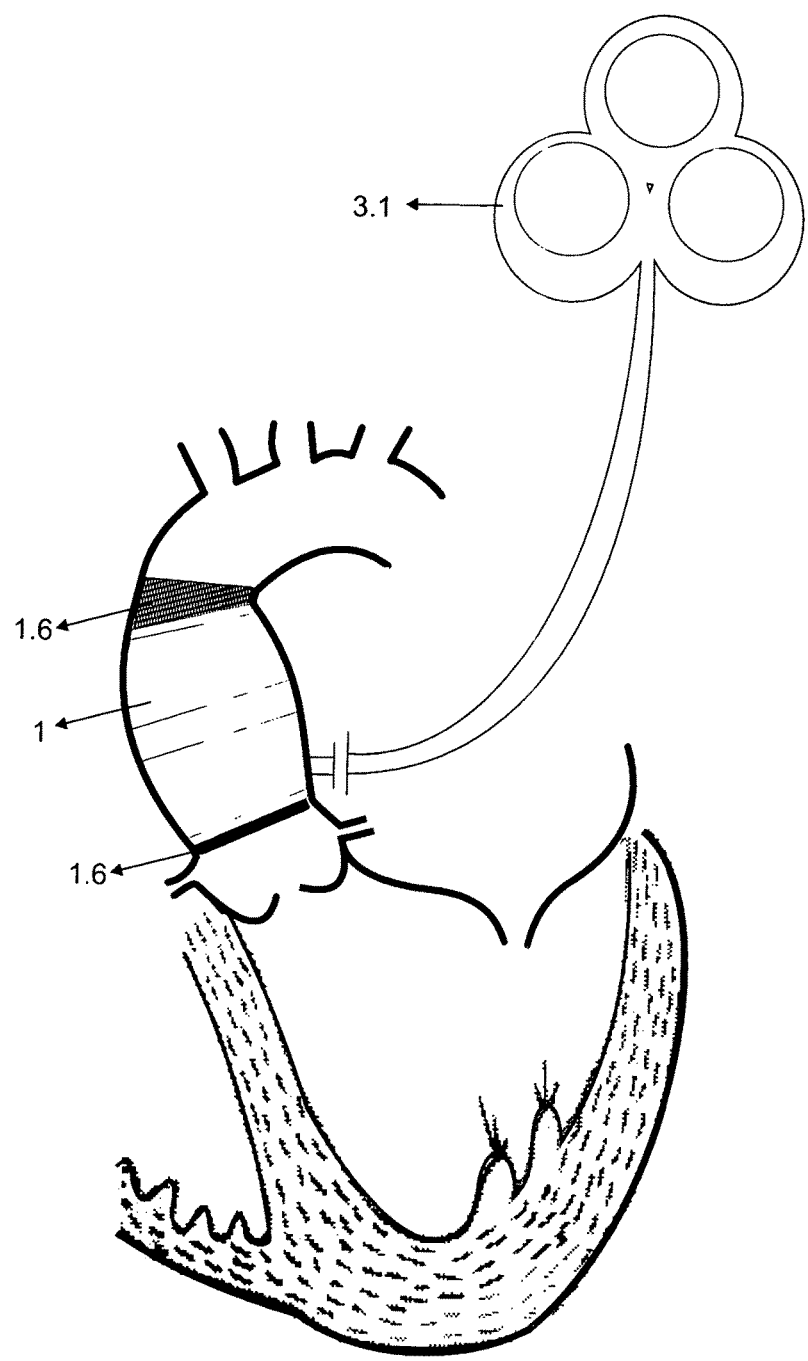
FIG. 1 The View of the Mounted Endovascular Heart Assist Device System on the Heart Cross Section FIG. 2 Overview of the Endovascular Heart Assist Device System FIG. 3 Assembled View of the Apparatus Interior the Body FIG. 4 Assembled View of Apparatus Exterior the Body FIG. 5 Rear View of the Control Unit FIG. 6 The View of the Control Unit with the Opened Cover FIG. 7 The View of the Control Unit Cover and Outdoor Power Transmission Unit FIG. 8 Motor Section View FIG. 9 The Exploded View of the Engine Provision of track numbers of the figures is given below;
1. Endovascular Heart Assist Device.
    1.1. Blood Pump Engine
        1.1.1. Turbulence Relief Wings (diffuser)
        1.1.2. Input Piece
        1.1.3. Output Part
    1.2. Rotor
        1.2.1. Helical propeller blades
    1.3. Stator
        1.3.1. Electric coils
    1.4. Magnetic bearings
    1.5. Roller Bearing
    1.6. Wire Cage
2. Control Unit
    2.1. Microprocessor
    2.2. Battery
    2.3. Back-up Battery
    2.4. Digital Display
    2.5. Adapter
3. Power Transmission Apparatus
    3.1. Internal Power Transfer Unit
    3.2. External Power Transfer Unit
Figure 2:
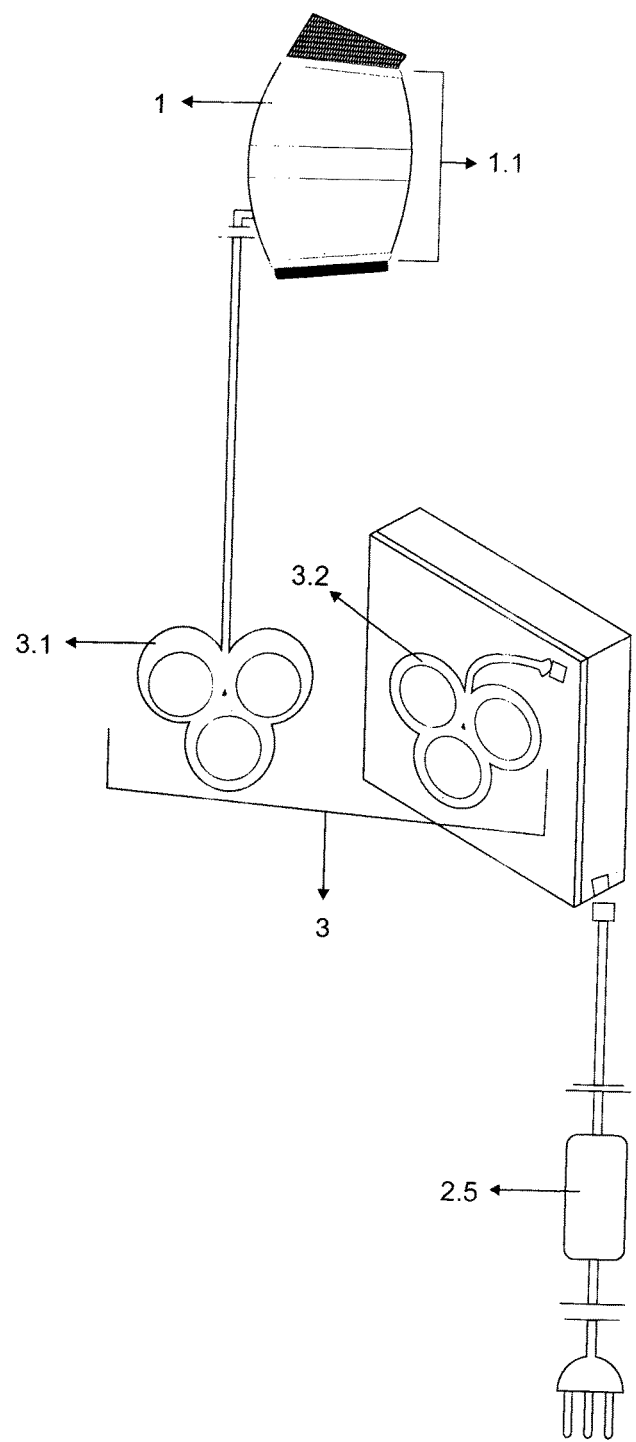
Figure 3:
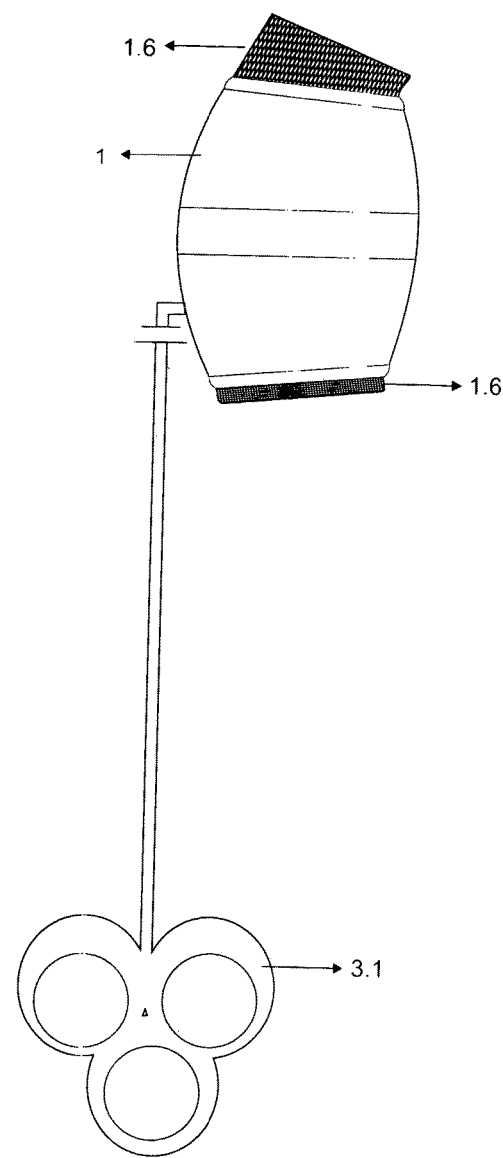
Figure 4:
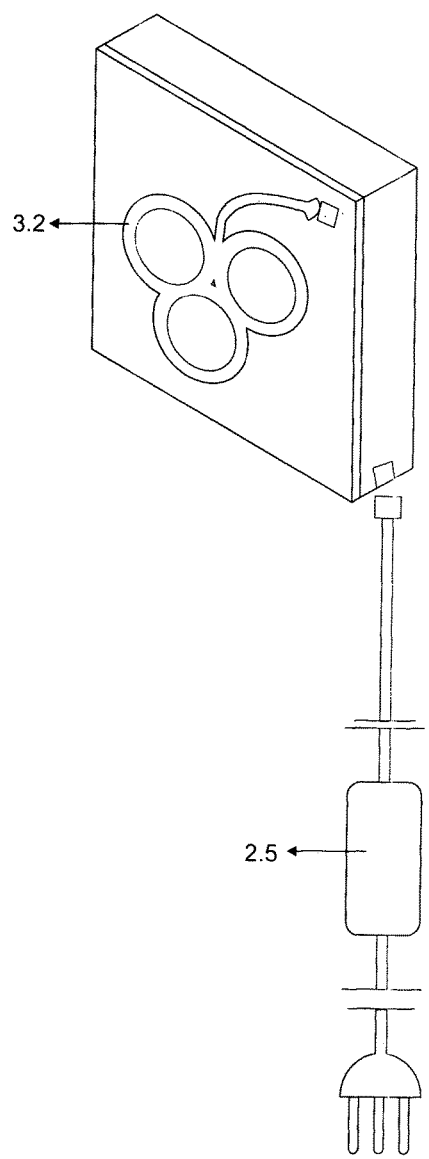
Figure 5:
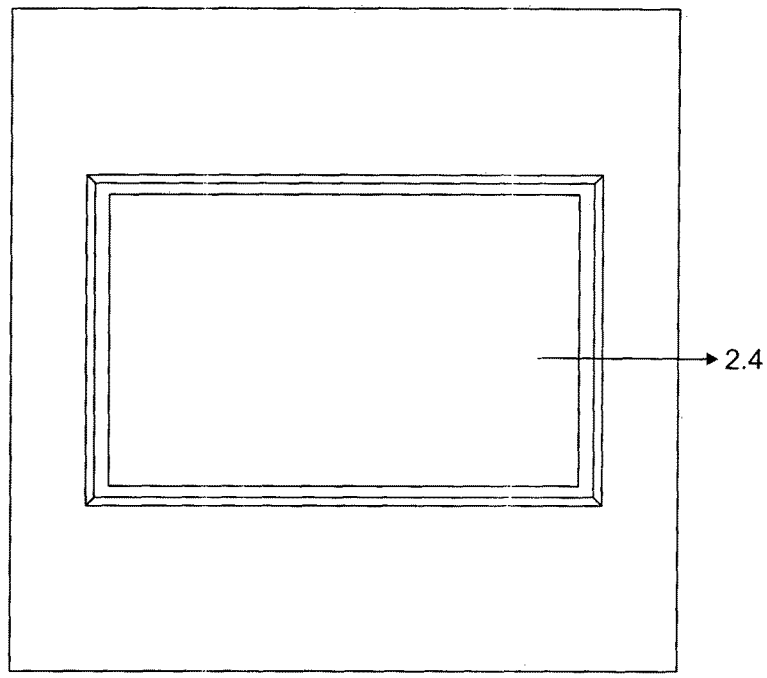
Figure 6:
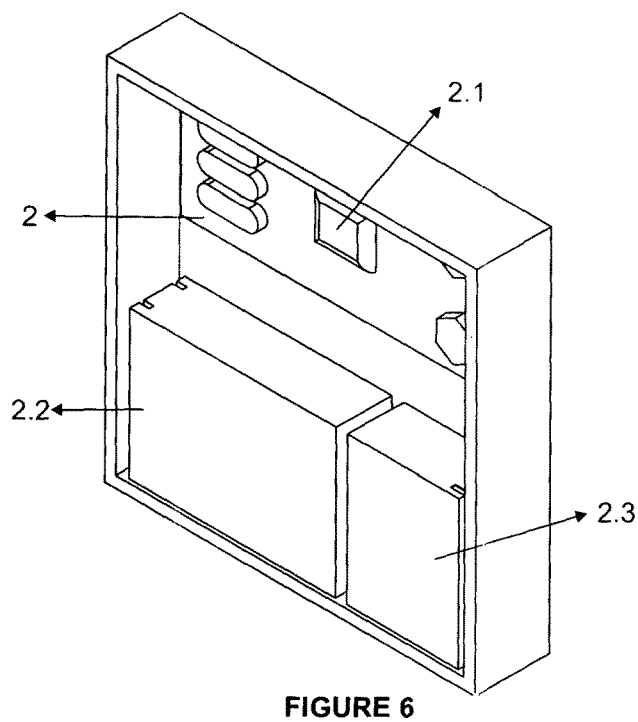
Figure 7:
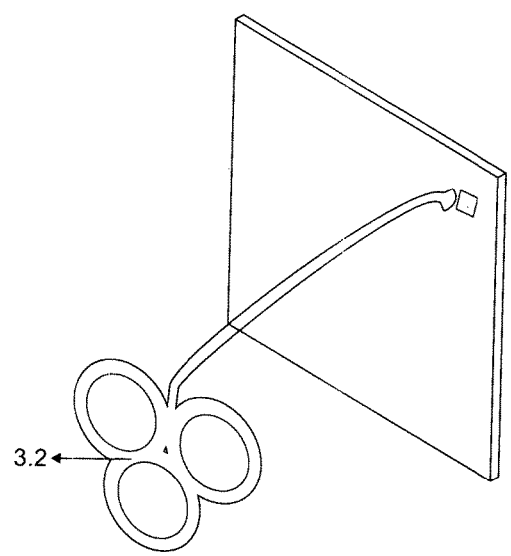
Figure 8:
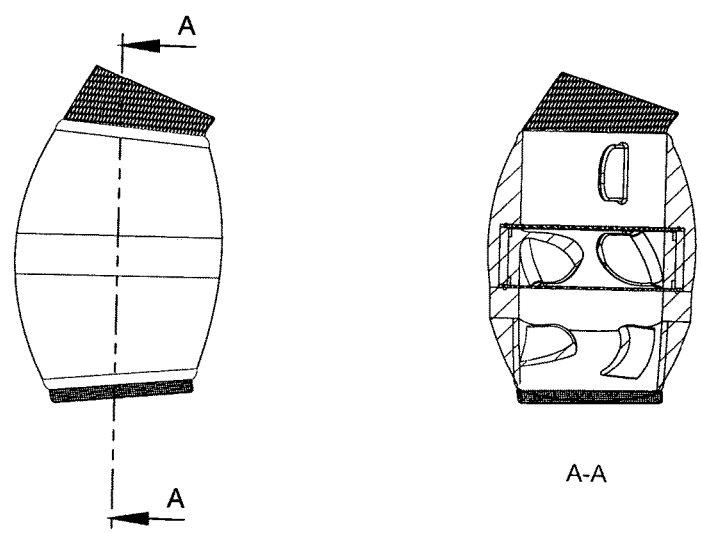
Figure 9:
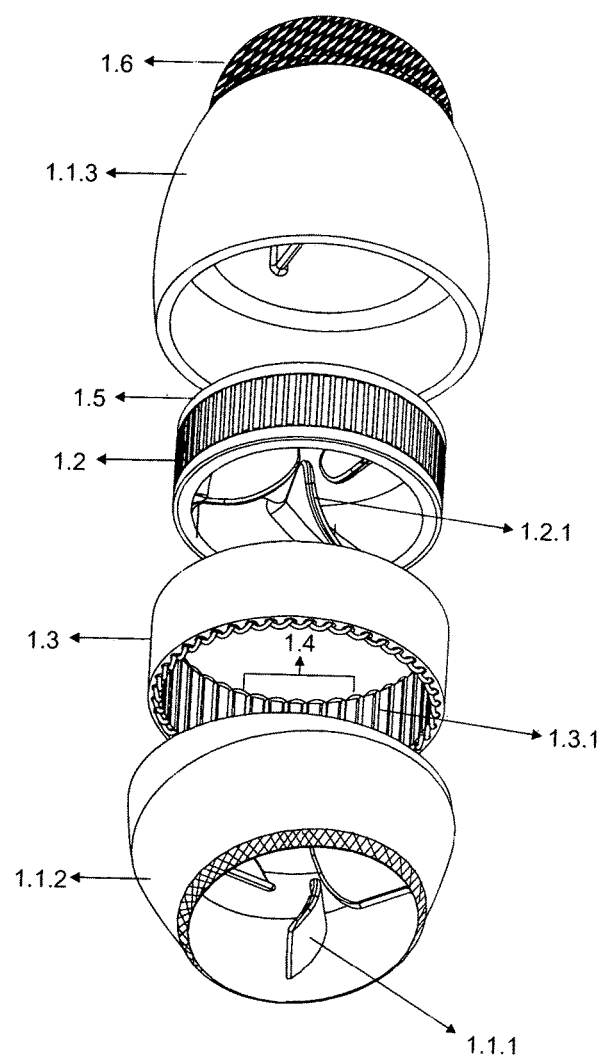

The invention is mainly composed of endovascular heart assist device (1), the control unit (2) and the wireless energy transfer apparatus (3). Endovascular heart assist device (1) is made up of the blood pump motor inside the device (1.1), the rotor (1.2), stator (1.3), the roller bearing (1.5) supported with magnetic bearing (1.4) and the wire cage (1.6) parts. The body of blood pump motor (1.1) consists of two parts; input (1.1.2) and the output part (1.1.3). Moreover, the input part (1.1.2) and the output part (1.1.3) contain propeller blades relieving turbulence (diffuser) (1.1.1). The rotor (1.2) comprises at least two helical propeller blades (1.2.1) without a pin (axis). Stator (1.3) includes electric coils (1.3.1) on it. The rotor (1.2) revolves freely with the propulsion received from this electrical coil (1.3.1) on the roller bearing (1.5) supported with magnetic bearing (1.4). Through rotation of the rotor (1.2), the helical propeller blades (1.2.1) propel the blood from the inlet section away to the output section of the pump motor (1.1). The control unit (2) consists of a microprocessor (2.1) a battery (2.2), a back-up battery (2.3), a digital display (2.4) and an adapter (2.5). Each of the coils that senses the three-phase current of internal power transfer unit (3.1) is placed under the skin of the patient in appropriate positions by the heart surgeon. Wireless energy transfer apparatus (3) performs three-phase wireless electrical energy transfer by transferring the power of all the three phases simultaneously from the external wireless energy transfer unit (3.2) into the internal energy transfer unit (3.1) wirelessly, and the electric energy required for the system is provided uninterruptedly from outside the body.

A backup battery (2.3) is available against any mishap that may occur in order to prevent the interruption of blood pump motor (1.1) running. The single-phase or three-phase current of mains electricity continuously charges the battery (2.3) and spare battery (2.3) through an adapter (2.5). The microprocessor (2.1) transforms the direct current which it receives from the battery (2.2) into the three-phase AC current. Then the external power transfer unit (3.2) simultaneously transfers all three-phases of alternating current to the internal power transfer unit (3.1) wirelessly. Each of the coils that senses the three-phase current of internal power transfer unit (3.1) is placed under the skin of the patient in appropriate positions by the heart surgeon. The coils of external power transfer unit (3.2) are designed in accordance with the position of internal power transfer unit (3.1) coils.

Some of the diseases accompanied by severe heart failure can partially or completely heal. When the assist device is not requited, it is surgically removed. If there is no expected improvement in the patient heart a heart assist device will remain attached during the lifetime of a patient, and it will continue to run and assist the heart until the end of patient's life.

In order to install the heart assist device to the artery as we mentioned about it in the national patent application numbered TR2012/00951 and Patent Cooperation Treaty application numbered PCT/TR2012/00055 we had made before, as also can be understood from documents, the artery is cut completely from a certain place, and either side of the two cuts is stitched transarterially to the input and output section of the heart assist device. When the documents are examined, it will occur that this device is too large to be placed into the vessel, and it is also a one-piece device integrated with its rotor and stator.

This endovascular heart assist device (1), the subject of our invention, is located entirely within the artery. The rotor with (1.2) helical propeller blades (1.2.1) rotates freely on the roller bearing (1.5) supported with the magnetic bearing (1.4) in arteries without contacting arteries. Magnetic bearing (1.4), which is constructed by permanent magnet bars and rings made of Neodymium, support magnetic roller bearings (1.5). The magnetic field that rotates the rotor (1.2) is formed by the current flowing through the electrical coils (1.3.1) located on the stator (1.3). The stator (1.3) is made of overlapped silicone sheet metal, and there are bores on it and electric coils (1.3.1) are located in that bores. Rotor (1.2) is hollow and includes at least two helical propeller blade on the skeleton (1.2.1).

The speed of the rotor rotation will be adjusted in real time by the microprocessor (3.4) with the synchronized analysis of the ECG signals received from the skin electrode, and as a result, when the heart assist device processes the received signals, it will run simultaneously with heart and the rate will increase or decrease along with them. When the ECG signals are not technically feasible, there are intense parasites or in case of irregular heart rhythm, (arrhythmia, irregular heartbeat, too fast or too slow heart beats, etc.), the pre-determined and recorded rotation speed of the engine by the doctor according to the patient's condition will be selected and implemented by the microprocessor (3.4) automatically.

Blood pressure will be monitored continuously through arm sphygmomanometer and the data obtained will be processed with the artificial intelligence and optimal rotor speed be determined with the help of the software, and these adjustments will be carried out manually.

Sphygmomanometer will not remain permanently in the arm, because it will be removed when the proper blood flow value for the patient is determined.

In a healthy person, the heart flow increases with the increase of heart rate. However, the only variable is not heart rate per minute. In a healthy person, "systolic ejection time" is also extended together with systolic loading. Therefore, while heart rate per minute is increased when the cardiac output flow is required to increase, software including the appropriate algorithms that increase systolic ejection time, that is "systolic time interval" should be prepared.

When the blood flow of the cardiac support device is required to increase, the heart rate and systolic ejection time must be increased manually together or separately. As this cardiac support device comprises asynchronous motors, it is only possible to change, increase or decrease the speed of the engines by changing the frequency of the alternating current which feeds the motor. Therefore, the frequency of the alternating current or "rotation interval" of the motor in systole should be increased in order to enhance blood flow rate of the support device. Both variables should be tested separately or together in the R & D stage in order to achieve the ideal system of this cardiac support device. Blood pumps of the heart assist device run synchronous with the ECG signal from the heart. As is known, these signals are produced in the sinus node in the right atrium of the heart with the effects of many mechanical, biochemical and endocrine feedback mechanisms associated with the circulatory system. While the signals accelerate in case of exertion, excitement, high fever, they decelerate in such cases as resting or sleep. Thus, the heart assist device will be connected to its natural microprocessor in the sinus node of the heart in a way, and the speed will accelerate during exertion and will slow down at rest. Therefore, it will be sufficient when the microprocessor of the device increases or decreases systolic ejection time, that is, on/off time interval of blood pump engine rather than heart rate per minute in order to keep the sustainable cardiac output in balance during the day.

Thanks to the magnetic bearing formed by permanent neodymium magnet rings located on both sides of the stator and rotor, the device is made to run safely in the place where the rotor and the stator is located.

It is known that the outside of the devices such as a stent and septal occlude made of nickel-titanium alloy (nitilon) is covered by the intima layer and vascular endothelial cells in a short time after the placement of the devices. It is estimated that the apparatus (1) of our invention will also be covered naturally with the intima layer and vascular endothelial cells as a result of intimal proliferation, and the support device and artery are expected to adhere to each other. There will also be a stent-like, biocompatible wire cage (1.6) installed only externally in the front and back part or all parts of the support device. By inflating a balloon inside the wire cage (1.6), this device will be fixed to the artery wall tightly by a cardiac surgeon during a surgery. The inlet section of the support device has been planned to be fitted on the sinotubular junction, which is the narrowest part of the way out. This junction is regarded as the border between the aorta and heart. Thus, the contacting surface of blood with foreign material will be limited to only the surface of the spinning rotor, and this will not damage the cellular components of blood.

The apparatus inserted into the vein is applied without damaging the patient's cardiovascular physiology. Heart surgeon installs the system into the artery with a small incision in a suitable technique and then the incision spot is simply repaired and artery integrity is kept intact. This heart assist device will provide pulsatile blood flow in patients by starting, stopping or slowing down synchronically with the ECG signals received from the skin electrodes of the patients. Pulsatile blood flow has many advantages in the tissue flushing compared to continuous flow.

Corners have been designed as filleting in order to prevent the development of blood clots on the corner surfaces. Micro flaps or channels can be added outside the rotor to prevent the development of blood clots.

The turbulence relieving propeller blades (1.1.1) exist on the motor (1) inlet (1.1.2) and the output part (1.1.3). The properties of these blades are that they are made of biocompatible a material with very good thermal conductivity. These flaps play an important role in removal of heat generated in the engine.

The rotor of the blood pump motor is made up of overlapped silicone sheet metal. Rotor (1.2) comprises bars and rings in the shape of a squirrel-cage made of electrically conductive metals such as copper, aluminum or gold or alloys.

In addition, all apparatuses have been insulated with a nonconductive insulating material, and electricity leakage is out of question. Insulation has been made with a poor conductive material to prevent the damage of the heat around. In addition, there is a biocompatible layer outside of the heart assist device to damp vibration.

The invention claimed is:

1. An endovascular heart assist device, comprising:
a wireless energy transfer apparatus which comprises an internal energy transfer unit being configured to be placed under the skin of a patient, and an external energy transfer unit being configured to be located outside the body of the patient and being configured to transfer electrical energy into the internal energy transfer unit wirelessly, wherein the internal energy transfer unit does not comprise an internal electronics and battery module; and
a brushless blood pump motor which comprises a stator and a rotor, wherein the stator comprises an electric coil being configured to receive the electrical energy from the internal energy transfer unit by wire or wirelessly, and the rotor is rotatively supported within the stator, configured to revolve freely with the propulsion received from the electrical coil, and the rotor comprises at least two helical propeller blades extending inside from sidewalls of the rotor, wherein the two helical propeller blades propel the blood in an artery;
wherein the endovascular heart assist device is installed in wide parts of root portions of main pulmonary artery and aorta after leaving a heart.

2. The endovascular heart assist device of claim 1, wherein the stator comprises a magnetic bearing, and the rotor comprises a roller bearing rotatively supported by the magnetic bearing.

3. The endovascular heart assist device of claim 2, wherein the magnetic bearing is formed of permanent magnet bars and rings.

4. The endovascular heart assist device of claim 3, wherein the electric coil is located in the gaps of the permanent magnet bars and rings.

5. The endovascular heart assist device of claim 1, wherein the brushless blood pump motor comprises an inlet part and an outlet part, both comprising at least two turbulence relieving propeller blades, wherein the stator is located between the inlet part and the outlet part.

6. The endovascular heart assist device of claim 5, further comprising a biocompatible wire cage installed externally on the inlet part and the outlet part to immobilize the motor in the artery, wherein a balloon is disposed inside the biocompatible wire cage and the balloon is inflated to fix the endovascular heart assist device to the artery wall tightly.

7. The endovascular heart assist device of claim 1, wherein the electrical energy of three phases is transferred from the external power transfer unit to the internal power transfer unit.

8. The endovascular heart assist device of claim 1, wherein the interior power transfer unit contains a backup battery which is configured to supply power to the electric coil if the electrical energy transmission from the external power transfer unit to the internal power transfer unit is stopped.

9. The endovascular heart assist device of claim 1, further comprising a biocompatible layer formed outside of the device which helps to damp the vibration of the motor in the artery.

10. The endovascular heart assist device of claim 1, further comprising a microprocessor which increases or decreases systolic ejection time, that is, on/off time interval of the blood pump motor rather than heart rate in order to keep a sustainable cardiac output in balance during the day.

11. An endovascular heart assist device, comprising:
a brushless blood pump motor which comprises at least two hollow and helical propeller blades without a pin (axis) in an inner wall of the brushless blood pump motor;
at least one stator;
at least one rotor fixed inside the at least one stator, wherein the rotor does not have a rotating shaft and the rotor is configured to rotate freely on a roller bearing;
a magnetic bearing which is constructed by permanent magnetic bars and rings, wherein the magnetic bearing supports the roller bearing; and
wherein the at least one stator configured to produce a magnetic field, wherein the magnetic field enables the rotation of the rotor;
wherein the endovascular heart assist device is installed in wide parts of root portions of main pulmonary artery and aorta after leaving a heart.

12. The endovascular heart assist device of claim 11, wherein the rotor is formed with overlapped silicone metal sheets, and contains squirrel cage-shaped bars and rings made of electrically conducting metals.

13. The endovascular heart assist device of claim 11, wherein an inlet and an output element of the blood pump motor contain a plurality of turbulence relieving propeller blades which eliminate turbulence that may occur in the blood.

14. The endovascular heart assist device of claim 11, wherein the blood pump motor is asynchronous and comprises a squirrel-cage rotor;
wherein a required three-phase electric energy for the operation of motor is transmitted wirelessly from a three-phase external power transfer unit into an internal power transfer unit.

15. The endovascular heart assist device of claim 14, wherein a power transmission unit transfers the three phases altogether at the same time from the external power transfer unit to the internal power transfer unit through three separate wireless links.

16. The endovascular heart assist device of claim 15, wherein the power transmission unit contains the internal power transfer unit that transfers three-phase electric energy transmitted by the external power transfer unit into the blood pump.

17. The endovascular heart assist device of claim 15, wherein the power transmission unit contains a backup battery which will continue to supply power to the motor if the power transmission from the internal power transfer unit stops.

18. The endovascular heart assist device of claim 11, further comprising a biocompatible wire cage which is only installed externally in a front and back part of the endovascular heart assist device or entire endovascular heart assist device to immobilize the endovascular heart assist device in the artery, wherein a balloon is disposed inside the biocompatible wire cage and the balloon is inflated to fix the endovascular heart assist device to the artery wall tightly.

19. The endovascular heart assist device of claim 11, further comprising a biocompatible layer which helps to damp a vibration by forming a layer outside of the device.

20. The endovascular heart assist device of claim 11, further comprising a microprocessor which increases or decreases systolic ejection time, that is, on/off time interval of the blood pump motor rather than heart rate in order to keep a sustainable cardiac output in balance.

\* \* \* \* \*